United States Patent
Yuan

(10) Patent No.: US 10,989,425 B2
(45) Date of Patent: Apr. 27, 2021

(54) HUMIDIFICATION DEVICE AND HUMIDIFICATION METHOD

(71) Applicant: BOE TECHNOLOGY GROUP CO., LTD., Beijing (CN)

(72) Inventor: Zuo Yuan, Beijing (CN)

(73) Assignee: BOE TECHNOLOGY GROUP CO., LTD., Beijing (CN)

( * ) Notice: Subject to any disclaimer, the term of this patent is extended or adjusted under 35 U.S.C. 154(b) by 0 days.

(21) Appl. No.: 15/551,544

(22) PCT Filed: Jan. 5, 2017

(86) PCT No.: PCT/CN2017/070222
§ 371 (c)(1),
(2) Date: Aug. 16, 2017

(87) PCT Pub. No.: WO2017/181739
PCT Pub. Date: Oct. 26, 2017

(65) Prior Publication Data
US 2019/0032935 A1    Jan. 31, 2019

(30) Foreign Application Priority Data

Apr. 22, 2016    (CN) .......................... 201610258421.3

(51) Int. Cl.
*F24F 6/14*    (2006.01)
*F24F 6/00*    (2006.01)
(Continued)

(52) U.S. Cl.
CPC .................. *F24F 6/14* (2013.01); *F24F 6/00* (2013.01); *G01N 27/223* (2013.01);
(Continued)

(58) Field of Classification Search
CPC ..... A61F 9/0026; A61B 5/443; A61B 5/0077; A61B 5/0537; F24F 6/14; F24F 6/00;
(Continued)

(56) References Cited

U.S. PATENT DOCUMENTS 8,182,425 B2 *    5/2012  Stamatas ............... A61B 5/0059
                                                  600/306
8,652,042 B2 *    2/2014  Mattoli ................. A61B 5/4869
                                                  600/306
(Continued)

FOREIGN PATENT DOCUMENTS

CN    202281345 U    6/2012
CN    102889660 A    1/2013
(Continued)

OTHER PUBLICATIONS

First Office Action for Chinese Application No. 201610258421.3, dated Jul. 9, 2018, 8 Pages.
(Continued)

*Primary Examiner* — Stephen Hobson
(74) *Attorney, Agent, or Firm* — Brooks Kushman P.C.

(57) ABSTRACT

A humidification device and a humidification method are provided. The humidification device includes: an image acquisition module configured to acquire an image of a user skin; a processing module configured to determine a moisture content of the user skin based on the image and determine a spraying amount for humidifying an air based on the moisture content; and a humidification module configured to humidify the air based on the spraying amount.

11 Claims, 3 Drawing Sheets

(51) Int. Cl.
*G01N 27/22* (2006.01)
*A61B 5/00* (2006.01)
*F24F 120/00* (2018.01)
*A61B 5/0537* (2021.01)

(52) U.S. Cl.
CPC ........... *A61B 5/0077* (2013.01); *A61B 5/0537* (2013.01); *A61B 5/443* (2013.01); *F24F 2120/00* (2018.01)

(58) Field of Classification Search
CPC .... F24F 2120/00; F24F 2120/10; F24F 11/30; F24F 6/12; G01N 27/223; Y02B 30/54
See application file for complete search history.

(56) References Cited

U.S. PATENT DOCUMENTS

| | | | | |
|---|---|---|---|---|
| 10,152,529 | B2* | 12/2018 | Hyde | G16H 20/13 |
| 10,195,076 | B2* | 2/2019 | Fateh | A61F 9/0026 |
| 2010/0126197 | A1* | 5/2010 | Nakaguro | B60H 3/02 |
| | | | | 62/271 |
| 2015/0054944 | A1* | 2/2015 | Bangera | A61B 5/443 |
| | | | | 348/135 |
| 2016/0015470 | A1* | 1/2016 | Border | A61B 17/00 |
| | | | | 600/117 |
| 2016/0270656 | A1* | 9/2016 | Samec | G02B 27/0093 |
| 2017/0112666 | A1* | 4/2017 | Fateh | A61B 3/0083 |
| 2017/0156594 | A1* | 6/2017 | Stivoric | A61B 5/6808 |
| 2017/0189637 | A1* | 7/2017 | Fateh | A61M 16/0683 |
| 2017/0303783 | A1* | 10/2017 | Yang | A46B 15/0022 |
| 2019/0046044 | A1* | 2/2019 | Tzvieli | G02B 27/017 |
| 2019/0388021 | A1* | 12/2019 | McLellan | G01J 1/4204 |
| 2020/0060609 | A1* | 2/2020 | Bock | A61B 5/1477 |
| 2020/0176099 | A1* | 6/2020 | Welss | A61B 5/443 |

FOREIGN PATENT DOCUMENTS

| | | |
|---|---|---|
| CN | 103900195 A | 7/2014 |
| CN | 104434038 A | 3/2015 |
| CN | 104586364 A | 5/2015 |
| CN | 105387563 A | 3/2016 |
| CN | 105928116 A | 9/2016 |
| JP | 3864385 B2 | 12/2006 |
| JP | 2008281277 A | 11/2008 |
| JP | 2011242043 A | 12/2011 |

OTHER PUBLICATIONS

1$^{st}$ Chinese Office Action, English Translation.
CN105387563A, English Abstract and Translation.
JP2011242043A, English Abstract and Translation.
International Search Report and Written Opinion for Application No. PCT/CN2017/070222, dated Apr. 11, 2017, 10 Pages.

* cited by examiner

HUMIDIFICATION DEVICE AND HUMIDIFICATION METHOD

CROSS-REFERENCE TO RELATED APPLICATIONS

This application is the U.S. national phase of PCT Application No. PCT/CN2017/070222 filed on Jan. 5, 2017, which claims priority to Chinese Patent Application No. 201610258421.3 filed on Apr. 22, 2016, the disclosures of which are incorporated in their entirety by reference herein.

TECHNICAL FIELD

The present disclosure relates to the field of air humidification, and in particular to a humidification device and a humidification method.

BACKGROUND

Skin is a natural outerwear of a human body and functions as an important barrier. A cuticle at an outermost layer of the skin and a sebum film on the cuticle may prevent a water loss of the skin. Normally, a moisture content of the cuticle is about 10%, and it is indicated that the skin lacks moisture if such moisture content is smaller than 10%.

The sebum and water secreted by the skin may be decreased gradually in autumn and winter, and the skin may become dim, rough, and accordingly the skin may be cracked and scratchy. Especially for the people who need to work on computer for a long time and the middle-aged and aged people, the skin may become worse due to a large water loss of skin. Therefore, a daily skin moisturization is very important.

At present, a humidification device is an important means to keep the skin of a fine humidity. However, the humidification device in the related art does not have many functions, and especially a spraying amount needs to be adjusted manually by a user through an observation. Although some more advanced humidification devices can adjust the spraying amount dynamically according to air humidity, the users have different physical qualities, i.e., the air humidity for the users to keep their skin of a fine state are different. Therefore, in the related art, it is not able to perform the air humidification according to the status of the user skin.

SUMMARY

The objective of the present disclosure is to provide a humidification solution to guarantee a healthy level of moisture content of a user skin.

To achieve the above objective, a humidification device is provided in the present disclosure, including:

an image acquisition module, configured to acquire an image of a user skin;

a processing module, configured to determine a moisture content of the user skin based on the image and determine a spraying amount for humidifying an air based on the moisture content; and a humidification module, configured to humidify the air based on the spraying amount.

Optionally, the image acquisition module includes:

an image capturing unit, configure to capture at least one candidate image of the user skin;

a selection unit, configured to select, based on definition of the at least one candidate, one candidate image as the image for determining the moisture content of the user skin.

Optionally, the processing module includes:

an identification unit, configured to identify a specific region of the image corresponding to a user face;

an image analysis unit, configured to determine the moisture content of the user skin based on an image parameter of the specific region.

Optionally, the image parameter includes at least one of color brightness and a smoothness degree.

Optionally, the processing module further includes:

a storage unit, configured to store a correspondence between the moisture content of the user skin and the spraying amount;

a processing unit, configured to determine the spraying amount for humidifying the air by the humidification module based on the moisture content of the user skin and the correspondence.

Optionally, the humidification device further includes a manual control module configured to adjust the spraying amount for humidifying the air by the humidification module in response to a user operation.

Optionally, the humidification device further includes an update module configured to update the spraying amount corresponding to the moisture content of the user skin stored by the storage unit to a spraying amount determined in response to the user operation.

Optionally, the image acquisition module is configured to acquire the image of the user skin periodically, the processing module is configured to determine a current moisture content of the user skin based on a latest image of the user skin, and determine the spraying amount for humidifying the air based on the current moisture content of the user skin. The humidification device further includes a self-adaptive adjustment module configured to increase the spraying amount stored in the storage unit and corresponded to a previous moisture content of the user skin determined by the processing module in the case that the current moisture content of the user skin redetermined by the processing module is smaller than a threshold after the humidification module humidifies the air based on the spraying amount.

Optionally, the humidification device further includes a display module configured to display the moisture content of the user skin.

A humidification method is further provided in the present disclosure, including:

acquiring an image of a user skin;

determining a moisture content of the user skin based on the image and determining based on the moisture content a spraying amount for humidifying an air; and humidifying the air based on the spraying amount.

Optionally, the determining the moisture content of the user skin based on the image includes:

identifying a specific region of the image corresponding to a user face;

determining the moisture content of the user skin based on an image parameter of the specific region.

Optionally, the image parameter includes at least one of color brightness and a smoothness degree.

Optionally, the determining the moisture content of the user skin includes:

quantizing the color brightness of the specific region to obtain the moisture content of the user skin, in the case that the image parameter consists of the color brightness; or the determining the moisture content of the user skin includes quantizing the smoothness degree of the specific region to obtain the moisture content of the user skin, in the case that the image parameter consists of the smoothness degree; or the determining the moisture content of the user skin includes normalizing the color brightness and the smoothness degree of the specific region, calculating a weighted sum of a normalized color brightness and the smoothness degree, and quantizing the weighted sum to obtain the moisture content of the user skin, in the case that the image parameter consists of the color brightness and the smoothness degree.

Optionally, the humidification method further includes:

redetermining the moisture content of the user skin after humidifying the air for a while;

increasing the spraying amount for humidifying the air in the case that the moisture content of the user skin is within a first value range;

decreasing the spraying amount for humidifying the air in the case that the moisture content of the user skin is within a second value range;

stopping humidifying the air in the case that the moisture content of the user skin is within a third value range, where the first value range is smaller than the second value range, and the second value range is smaller than the third value range.

A humidification device is further provided, including:

a housing;

a camera, arranged on the housing and configured to acquire an image of a user skin;

a processor, arranged within the housing and configured to determine a moisture content of the user skin based on the image and determine based on the moisture content a spraying amount for humidifying an air;

a display, arranged on the housing and configured to display the moisture content of the user skin; and a sprayer arranged within the housing, where a spray nozzle of the sprayer is arranged on the housing.

Optionally, the humidification device further includes a button arranged on the housing and configured to adjust the spraying amount for humidifying the air by a humidification module in response to a user operation.

According to the present disclosure, firstly the image of the user skin is quantized to obtain the current moisture content of the user skin, and then the spraying amount is determined based on the current moisture content of the user skin to humidify the air, so as to make the current air humidity to meet the health requirement of the user skin. Obviously, compared with the related art, the humidification method in the present disclosure may meet the humidification requirements of the users having different skin characteristics, which has a high applicability and practical value.

DETAILED DESCRIPTION

In order to make the technical issues, the technical solutions and the advantages of the present disclosure more apparent, the present disclosure will be described hereinafter in detail in conjunction with the drawings and embodiments.

In views of the technical issue that the humidification device in the related art cannot humidity the air dynamically according to the moisture content of the user skin, the present disclosure provides a technical solution.

Figure 1:
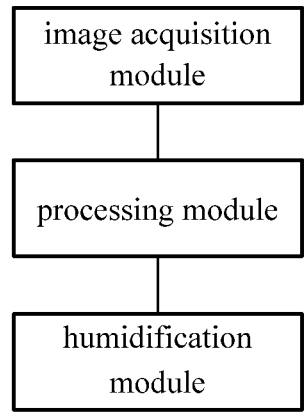
FIG. 1 is a schematic view of a humidification device in the present disclosure.

Firstly, a humidification device as shown in FIG. 1 is provided in some embodiments of the present disclosure, including:

an image acquisition module, configured to acquire an image of a user skin;

a processing module, configured to determine a moisture content of the user skin based on the image and determine a spraying amount for humidifying an air based on the moisture content; and a humidification module, configured to humidify the air based on the spraying amount.

The humidification device in some embodiments of the present disclosure may adjust the spraying amount for humidifying the air based on the moisture content of the user skin, thereby guaranteeing a healthy state of the user skin. Therefore, the humidification device has a high applicability and practical value.

To be specific, the image acquisition module in some embodiments of the present disclosure includes:

an image capturing unit, configure to capture at least one candidate image of the user skin;

a selection unit, configured to select, based on definition of the at least one candidate, one candidate image as the image for determining the moisture content of the user skin.

It can be seen from the above description, a plurality of shot candidate images may be compared with each other, and the image with the highest definition is selected to determine the moisture content of the user skin, thereby guaranteeing an accurate result.

To be specific, when the moisture content of the user skin is low, the skin may become dim and rough. Taking advantage of this, the present disclosure provides a solution to effectively determine the moisture content of the user skin based on the image of the user skin.

In some embodiments of the present disclosure, the processing module includes:

an identification unit, configured to identify a specific region of the image corresponding to a user face;

an image analysis unit, configured to determine the moisture content of the user skin based on an image parameter (e.g., color brightness and/or smoothness degree) of the above specific region.

In a practical application, the identification module may select a portion of the image corresponding to the user face and take a region of a certain area (e.g. 2 cm×2 cm) with a low pixel color difference as the specific region. According the above method, it is able to avoid selecting a portion with a segment gap (e.g., eyes and nose) and prevent the moisture content calculation from being adversely affected by the shaded region.

When the specific region is of a dim color and a low smoothness degree, the user skin may lack of water. Similarly, when the specific region is of a bright color and a high smoothness degree, the user skin may be full of water.

In a practical application, the image analysis unit quantizes the moisture content of the user skin based on the color brightness and/or smoothness degree of the specific region. The specific region represents the skin of the user face, so the brighter the color of the region is and/or the smoother the region is, the higher the moisture content of the user skin may be. Otherwise, the dimmer the color of the region is and/or the rougher the region is, the lower the moisture content of the user skin may be.

Of course, the humidification device in some embodiments may further determine the spraying amount reasonably according to the air humidification requirement of the user.

The above processing module further includes a storage unit and a processing unit.

The storage unit is configured to store a correspondence between the moisture content of the user skin and the spraying amount.

For example, the lower the moisture content of the user skin is, the larger the spraying amount may be. Similarly, the higher the moisture content of the user skin is, the smaller the spraying amount may be.

The processing unit is configured to determine the spraying amount for humidifying the air by the humidification module based on the determined moisture content of the user skin and the above correspondence.

Based on the above storage unit and the processing unit, the humidification device in some embodiments of the present disclosure may create different data bases for different users. That is, the humidification device may store the humidification preference of many users. In a practical application, the user may firstly activate, through the humidification device, configuration information stored in the storage unit corresponding to the user himself, then the processing unit acquires from the storage unit the correspondence between the skin humidity and the spraying amount of the user himself, and controls the humidification module to select the spraying amount according to the humidification preference conforming to the correspondence.

In addition, in order to further meet the air humidity requirement of the user, the humidification device in some embodiments of the present disclosure may further include a manual control module configured to adjust the spraying amount for humidifying the air by the humidification module in response to a user operation.

By the above design, when the user is not satisfied with the spraying amount adjusted automatically by the humidification device, the user is able to adjust the spraying amount manually as needed. Based on this, the humidification device in the embodiment of the present disclosure may further learn the humidification preference of the user based on the user's adjustment operation, and thereby to modify the correspondence stored in the storage unit. To realize the above function, the humidification device in some embodiments of the present disclosure further includes an update module configured to update the spraying amount corresponding to the determined moisture content of the user skin stored by the storage unit to a spraying amount determined in response to the user operation.

It can be seen that, based on the above solution, the humidification device in some embodiments of the present disclosure may learn the humidification requirement of the user adaptively and meet the humidification preference of the user in a more intelligent manner, and thereby to provide a better user experience.

In addition, based on the above solution, the humidification device in some embodiments of the present disclosure may further adjust the correspondence stored in the storage unit on its own initiative in response to a change of the moisture content of the user skin after the air humidification. That is, the image acquisition module acquires the image of the user skin periodically, the processing module determines a current moisture content of the user skin based on a latest image of the user skin acquired by the image acquisition module, and determines the spraying amount for humidifying the air based on the current moisture content of the user skin.

Correspondingly, the humidification device in some embodiments of the present disclosure further includes a self-adaptive adjustment module configured to increase the spraying amount stored in the storage unit and corresponded to a previous moisture content of the user skin determined by the processing module in the case that the current moisture content of the user skin redetermined by the processing module is smaller than a threshold (i.e., the moisture content of the user skin in a healthy state) after the humidification module humidifies the air based on the spraying amount, and thereby to increase the spraying amount redetermined subsequently and make the air humidity to meet the requirement of the healthy user skin.

In addition, as an optional solution, the humidification device in some embodiments of the present disclosure may further include a display module configured to display the moisture content of the user skin, and thereby to make it convenient for the user to know the health state of the skin.

Next, the humidification device will be illustrated in conjunction with some embodiments.

Figure 2:
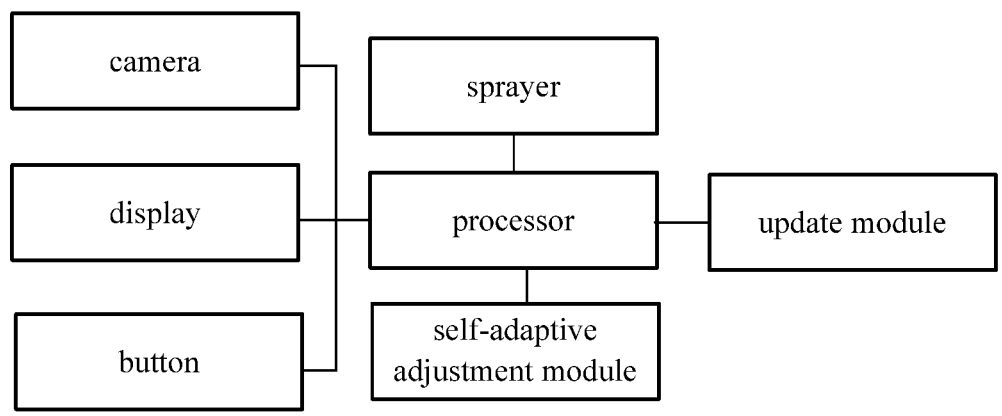
FIG. 2 is a schematic view of a humidification device in a practical application in the present disclosure.

As shown in FIG. 2, in some embodiments of the present disclosure, the humidification device mainly includes: a camera, a display, a button, a sprayer, a processor, an update module and a self-adaptive adjustment module.

The camera corresponds to the above image acquisition module, and configured to take a picture of the user skin periodically to acquire the image of the user skin.

The processor corresponds to the above processing module, which may analyze the image of the user skin and determine the moisture content of the user skin in real time subsequent to each shooting period. For example, assuming that the moisture content of the user skin is quantized to an order of magnitude from 0 to 100, in the case that color brightness of a specific region of the user face in the image is from 0 to 25, and a smoothness degree thereof is from 0 to 25, the processor may determine that the moisture content of the user skin is 30; in the case that the color brightness of the specific region of the user face in the image is from 75 to 100, and the smoothness degree thereof is from 75 to 100, the processor may determine that the moisture content of the user skin is 100.

After determining a level of the moisture content of the user skin, the processor controls the display to display the result to the user, and determines, based on the correspondence between the moisture content of the user skin and the spraying amount stored in the storage component (corresponding to the above storage unit), the spraying amount for humidifying the air by the sprayer. For example, in the case that the level of the moisture content of the user skin is in a range from 0 to 25, the spraying amount of the sprayer is 80%; in the case that the level of the moisture content of the user skin is in a range from 50 to 75, the spraying amount of the sprayer is 50%.

After then, the processor further controls the sprayer to humidify the air based on the determined spraying amount, so as to make air to reach to a healthy humidity required by the user skin.

In addition, the user may set by himself the correspondence stored in the storage unit through the button. For example, assuming that the level of the moisture content of the user skin in a range from 0 to 25 corresponds to the spraying amount of 80%, the user may reset the spraying amount through the button to increase the spraying amount to 100%.

Figure 3:
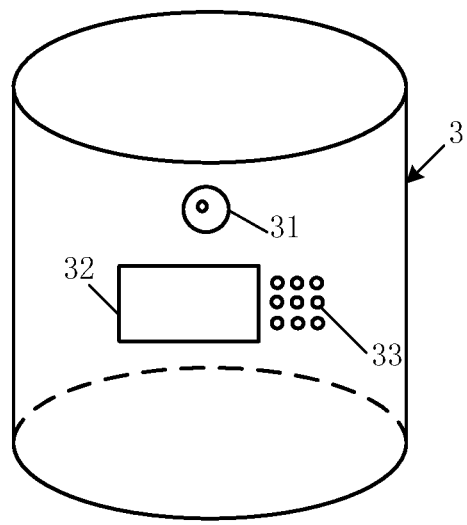
FIG. 3 is a schematic view of an exterior structure of a humidification device in the present disclosure.

In addition, as shown in FIG. 3, in some embodiments of the present disclosure, the humidification device has a housing 3, and the above camera 31, the display 32 and the button 33 are all arranged on the housing 3 for the user. When using the humidification device for the first time, the humidification device may control the spraying amount of the sprayer based on a default correspondence between the moisture content of the user skin and the spraying amount. Then, the user may adjust the spraying amount through the button 33 as needed, and generate in a self-adaptive manner a correspondence between a current moisture content of the user skin and the spraying amount determined in response to the user adjustment for a subsequent use; or the user may firstly set through the button 33 a correspondence between the moisture content of his own skin and the spraying amount, and then the sprayer may humidify the air based on the spraying amount set by the user himself.

After the humidification device humidifies the air for a while, in the case that a current spraying amount does not satisfy the user, the user may directly increase the spraying amount of the sprayer through the button 33. Then, the update module may modify the correspondence stored in the storage component in the processor in response to the user operation, and correspond the determined moisture content of the user skin with the spraying amount determined in response to the user operation, thereby making the humidification effect closer to the user' expectation.

In addition, in a next period of determining the moisture content of the user skin, in the case that the moisture content of the user skin still does not reach the healthy standard, it is indicated that the spraying amount determined based on the correspondence stored in the storage component cannot meet the user skin requirement. Correspondingly, the self-adaptive adjustment module may modify the correspondence stored in the storage component on its own initiative and increase the spraying amount corresponding to the moisture content of the user skin determined in the previous period, and thereby to improve the humidification effect gradually.

Compared with the related art, the humidification device in the present disclosure has the following advantage:

(1) the humidification device is able to humidify the air based on the moisture content of the user skin, and make the air humidity to meet the health requirement of the user skin;

(2) the users are able to set their respective correspondence between the moisture content of the skin and the spraying amount based on their own skin characteristics, thereby providing a personalized service, which has a good applicability;

(3) the sprayer amount of the humidification device may be adjusted in a self-adaptive manner according to a change of the moisture content of the user skin, thereby avoiding a resource waste and making the humidification device to work more efficiently;

(4) the user may adjust the spraying amount manually to modify the correspondence between the moisture content of the skin and the spraying amount, thereby making the humidification effect closer to the user' expectation;

(5) the moisture content of the user skin is monitored periodically, and the stored correspondence between the moisture content of the user skin and the spraying amount may be modified in the case that the spraying amount is not enough to make the moisture content of the user skin to reach the healthy standard, thereby improving the humidification effect gradually.

Figure 4:
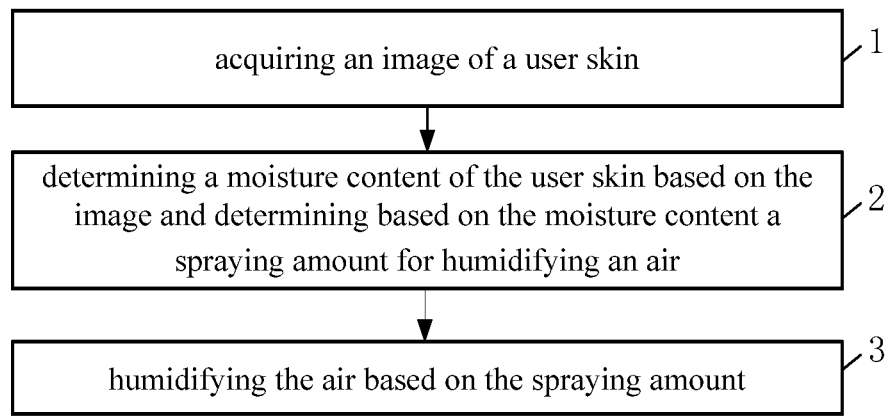
FIG. 4 is a flow chart of a humidification method in the present disclosure.

In another aspect, a humidification method is further provided in the present disclosure. As shown in FIG. 4, the method includes:

Step 1: acquiring an image of a user skin;

Step 2: determining a moisture content of the user skin based on the image and determining based on the moisture content a spraying amount for humidifying an air; and Step 3: humidifying the air based on the spraying amount.

According to the humidification method, firstly the image of the user skin is quantized to obtain the current moisture content of the user skin, and then the spraying amount is determined based on the current moisture content of the user skin to humidify the air, so as to make the current air humidity to meet the health requirement of the user skin. Obviously, compared with the related art, the humidification method in the present disclosure may meet the humidification requirements of the users having different skin characteristics, which has a high applicability and practical value.

To be specific, the above Step 2 may further include identifying a specific region of the above image corresponding to a user face; and determining the moisture content of the user skin based on an image parameter of the specific region.

Generally, skin glossiness may reflect the moisture content of the skin. Correspondingly, in the above Step 2, the moisture content of the user skin may be determined based on color brightness and/or a smoothness degree of the above specific region.

For example, in the case that the moisture content of the user skin is determined based on color data and smoothness degree data of the specific region, the determination of the moisture content of the user skin may include: normalizing the color brightness and the smoothness degree of the specific region to make them within an identical value range, calculating a weighted sum of a normalized color brightness and the smoothness degree, and quantizing the weighted sum to obtain the moisture content of the user skin. It should be noted that, in the case that the color brightness is more important than the smoothness degree for the determination of the moisture content of the user skin, a weighted value of the color brightness may be greater than a weighted value of the smoothness degree when calculating the weight sum thereof; otherwise, in the case that the smoothness degree is more important than the color brightness for the determination of the moisture content of the user skin, a weighted value of the smoothness degree may be greater than a weighted value of the color brightness when calculating the weight sum thereof.

For example, in the case that the moisture content of the user skin is determined merely based on the color brightness of the specific region, the determination of the moisture content of the user skin may include quantizing the color brightness of the specific region to obtain the moisture content of the user skin.

Similarly, in the case that the moisture content of the user skin is determined merely based on the smoothness degree of the specific region, the determination of the moisture content of the user skin may include quantizing the smoothness degree of the specific region to obtain the moisture content of the user skin.

Next, the humidification method will be illustrated by taking an example that the moisture content of the user skin is determined based both the color brightness and the smoothness degree.

Figure 5:
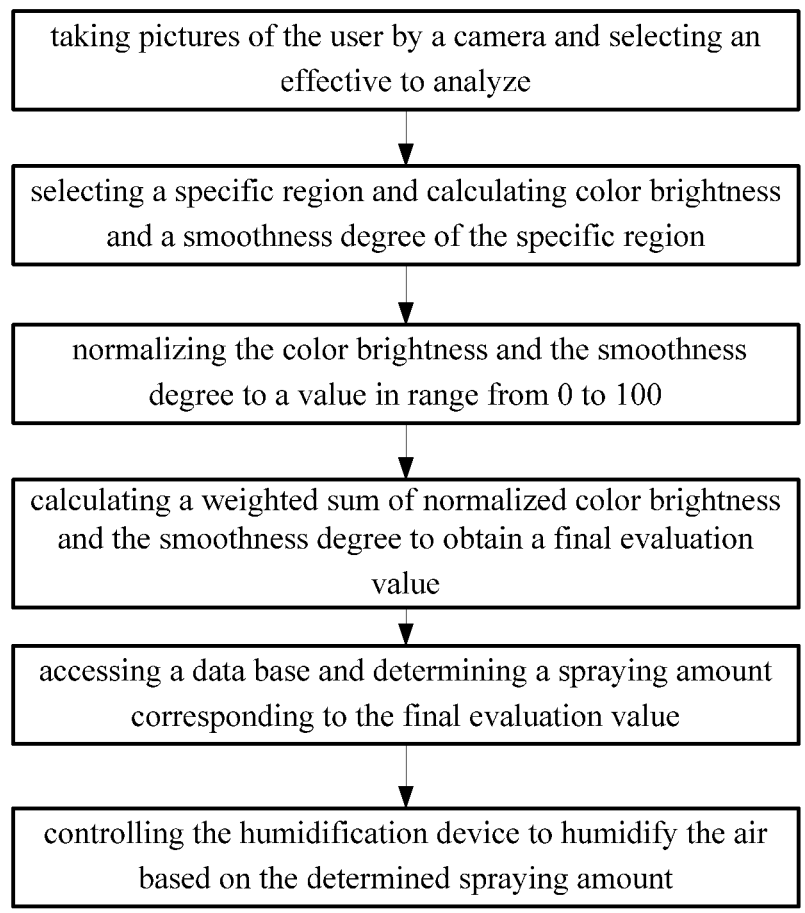
FIG. 5 shows a detailed flow of a humidification method in the present disclosure.

As shown in FIG. 5, according to the humidification method in some embodiments of the present disclosure, firstly the camera takes pictures of the user face periodically to acquire a plurality of candidate images, and then one candidate image is selected among the candidate images as an effective image based on definition of the candidate images and then analyzed.

A specific region of the effective image (i.e., a region of the image corresponding to the skin) is selected, and then color brightness and a smoothness degree of the specific region are calculated.

Then, the color brightness and the smoothness degree are normalized to a value in range from 0 to 100.

A weighted sum of normalized color brightness and the smoothness degree is calculated to obtain a final evaluation value. For example, in the case that the smoothness degree is more important than the color brightness for determining the moisture content of the user skin, a weighted value of the smoothness degree may be set to be ¾, and a weighted value of the color brightness may be set to be ¼. when calculating the weight sum thereof, the smoothness degree with a normalized value ¾ is added to the color brightness with a normalized value ¼.

After the final evaluation value is determined, a data base (may be stored in a storage component) is accessed, so as to search a spraying amount corresponding to the final evaluation value and humidifying the air based on the spraying amount.

In addition, in order to reduce the resource consumption, according to the humidification method in some embodiments of the present disclosure, the moisture content of the user skin may be retested after humidifying the air for a while, and the spraying amount may be modified in a self-adaptive manner based on improvement effect of the moisture content of the user skin.

To achieve the above effect, the moisture content of the user skin is divided into three value ranges, i.e., a first value range indicating that the user skin lacks of moisture, a second value range indicating that the moisture content of the user skin is close to a healthy standard, and a third value range indicating that the moisture content of the user skin has reaches or beyond the healthy standard. It should be noted that, the first value range is smaller than the second value range, and the second value range is smaller than the third value range.

The spraying amount may be increased in the case that the redetermined moisture content of the user skin is within the first value range, so as to improve the humidification effect and further improve the moisture content of the user skin.

The spraying amount may be decreased in the case that the redetermined moisture content of the user skin is within the second value range, so as to decrease an improving rate of the moisture content of the user skin and reduce the resource consumption.

The air humidification may be ceased in the case that the redetermined moisture content of the user skin is within the third value range.

It can be seen that, the humidification method in the present disclosure may adjust dynamically the spraying amount for the air humidification based on a real-time moisture content of the user skin.

The above are merely some embodiments of the present disclosure. A person skilled in the art may make further modifications and improvements without departing from the principle of the present disclosure, and these modifications and improvements shall also fall within the scope of the present disclosure.

What is claimed is:

1. A humidification device, comprising:
a button, configured to adjust a spraying amount for humidifying an air from a humidification module in response to a user operation when using a first correspondence to control the spraying amount; wherein the first correspondence is a default correspondence between a moisture content of a user skin and the spraying amount;
an update module, configured to update the spraying amount in the first correspondence to the spraying amount determined in response to the user operation; wherein the spraying amount determined in response to the user operation corresponds to an initial moisture content of the user skin, which forms a second correspondence; the initial moisture content of the user skin is determined by a processing module based on an initial image of the user skin acquired by an image acquisition module;
the image acquisition module, configured to acquire an image of the user skin periodically;
the processing module, configured to determine a current moisture content of the user skin based on a latest image and determine a spraying amount for humidifying the air based on the current moisture content of the user skin in a period; the current moisture content of the user skin and the spraying amount form a third correspondence; and
a humidification module, configured to humidify the air based on the spraying amount;
the processing module comprises:
a storage unit, configured to store a correspondence between different moisture contents of the user skin and spraying amounts, the correspondence comprises the first correspondence, the second correspondence and the third correspondence; and
a processing unit, configured to determine the spraying amount for humidifying the air from the humidification module based on the determined moisture content of the user skin and the correspondence;
the button, further configured to adjust the spraying amount for humidifying the air from the humidification module in response to a user operation;
the update module, further configured to update the spraying amount corresponding to the current moisture content of the user skin in the third correspondence to the spraying amount determined in response to the user operation, which forms a fourth correspondence;
wherein the humidification device further comprises:
a self-adaptive adjustment module, configured to increase the spraying amount in the fourth correspondence in the case that the current moisture content of the user skin redetermined by the processing module in a next period is smaller than a threshold.

2. The humidification device according to claim 1, wherein the image acquisition module comprises:
an image capturing unit, configure to capture at least one candidate image of the user skin; and
a selection unit, configured to select, based on definition of the at least one candidate, one candidate image as an image for determining the moisture content of the user skin.

3. The humidification device according to claim 1, wherein the processing module comprises:
an identification unit, configured to identify a specific region of the image of the user skin corresponding to a user face; and an image analysis unit, configured to determine the moisture content of the user skin based on an image parameter of the specific region.

4. The humidification device according to claim 3, wherein the image parameter comprises at least one of color brightness and a smoothness degree.

5. The humidification device according to claim 1, further comprising a display module configured to display the moisture content of the user skin.

6. A humidification method, comprising:
adjusting, by a button, a spraying amount for humidifying an air from a humidification module in response to a user operation when using a first correspondence to control the spraying amount; wherein the first correspondence is a default correspondence between a moisture content of a user skin and the spraying amount;
updating, by an update module, the spraying amount in the first correspondence to the spraying amount determined in response to the user operation; wherein the spraying amount determined in response to the user operation corresponds to an initial moisture content of the user skin, which forms a second correspondence; the initial moisture content of the user skin is determined by a processing module based on an initial image of the user skin acquired by an image acquisition module;
acquiring, by the image acquisition module, an image of the user skin periodically;
determining, by the processing module, a current moisture content of the user skin based on a latest image and determining, by the processing module, based on the current moisture content of the user skin, a spraying amount for humidifying the air in a period; the current moisture content of the user skin and the spraying amount form a third correspondence; wherein the processing module comprises: a storage unit, configured to store a correspondence between different moisture contents of the user skin and spraying amounts, the correspondence comprises the first correspondence, the second correspondence and the third correspondence; and a processing unit, configured to determine the spraying amount for humidifying the air from the humidification module based on the determined moisture content of the user skin and the correspondence; and
humidifying, by a humidification module, the air based on the spraying amount;
adjusting, by the button, the spraying amount for humidifying the air from the humidification module in response to a user operation;
updating, by the update module, the spraying amount corresponding to the current moisture content of the user skin in the third correspondence to the spraying amount determined in response to the user operation, which forms a fourth correspondence;
increasing, by a self-adaptive adjustment module, the spraying amount in the fourth correspondence in the case that the current moisture content of the user skin redetermined by the processing module in a next period is smaller than a threshold.

7. The humidification method according to claim 6, wherein
the determining the moisture content of the user skin based on the image comprises:
identifying a specific region of the image of the user skin corresponding to a user face; and
determining the moisture content of the user skin based on an image parameter of the specific region.

8. The humidification method according to claim 7, wherein the image parameter comprises at least one of color brightness and a smoothness degree.

9. The humidification method according to claim 8, wherein
the determining the moisture content of the user skin comprises quantizing the color brightness of the specific region to obtain the moisture content of the user skin, in the case that the image parameter consists of the color brightness; or
the determining the moisture content of the user skin comprises quantizing the smoothness degree of the specific region to obtain the moisture content of the user skin, in the case that the image parameter consists of the smoothness degree; or
the determining the moisture content of the user skin comprises normalizing the color brightness and the smoothness degree of the specific region, calculating a weighted sum of the normalized color brightness and smoothness degree, and quantizing the weighted sum to obtain the moisture content of the user skin, in the case that the image parameter consists of the color brightness and the smoothness degree.

10. The humidification method according to claim 9, further comprising:
redetermining the moisture content of the user skin after humidifying the air for a while;
increasing the spraying amount for humidifying the air in the case that the moisture content of the user skin is within a first value range;
decreasing the spraying amount for humidifying the air in the case that the moisture content of the user skin is within a second value range; and
stopping humidifying the air in the case that the moisture content of the user skin is within a third value range;
wherein the first value range is smaller than the second value range, and the second value range is smaller than the third value range.

11. The humidification device according to claim 1, wherein the image acquisition module is a camera, the processing module is a processor, and the humidification device further comprises:
a housing;
a display, arranged on the housing and configured to display the current moisture content of the user skin; and
a sprayer arranged within the housing, wherein a spray nozzle of the sprayer is arranged on the housing.

* * * * *